(12) United States Patent
Boudier

(10) Patent No.: US 12,134,778 B2
(45) Date of Patent: Nov. 5, 2024

(54) ANTI-ADHESION CULTURE MEDIUM

(71) Applicant: FERMENTALG, Livourne (FR)

(72) Inventor: Philippe Boudier, Cenon (FR)

(73) Assignee: FERMENTALG, Libourne (FR)

( * ) Notice: Subject to any disclaimer, the term of this patent is extended or adjusted under 35 U.S.C. 154(b) by 638 days.

(21) Appl. No.: 16/766,049

(22) PCT Filed: Nov. 23, 2018

(86) PCT No.: PCT/EP2018/082318
§ 371 (c)(1),
(2) Date: May 21, 2020

(87) PCT Pub. No.: WO2019/101899
PCT Pub. Date: May 31, 2019

(65) Prior Publication Data
US 2020/0347348 A1 Nov. 5, 2020

(30) Foreign Application Priority Data
Nov. 23, 2017 (FR) ...................................... 1761095

(51) Int. Cl.
*C12N 1/10* (2006.01)
*C12N 1/12* (2006.01)
*C12N 5/00* (2006.01)

(52) U.S. Cl.
CPC ............ *C12N 5/0018* (2013.01); *C12N 1/10* (2013.01); *C12N 1/12* (2013.01); *C12N 2500/22* (2013.01); *C12N 2500/24* (2013.01); *C12N 2533/30* (2013.01)

(58) Field of Classification Search
CPC .................................... C12N 1/10; C12N 1/12
See application file for complete search history.

(56) References Cited

U.S. PATENT DOCUMENTS

| 2002/0079270 | A1 | 6/2002 | Borodyanski |
| 2007/0227971 | A1* | 10/2007 | Denney ............... C12N 1/02 435/244 |
| 2013/0205850 | A1* | 8/2013 | Ganuza .............. A23K 50/40 71/23 |
| 2013/0309762 | A1 | 11/2013 | Sim et al. |

FOREIGN PATENT DOCUMENTS

| CN | 101979498 A | 2/2011 | |
| CN | 205241674 U | 5/2016 | |
| ES | 2351566 A1 * | 2/2011 | ............ C12M 21/02 |
| RU | 2603733 C1 | 11/2016 | |
| WO | 2014063229 A1 | 5/2014 | |
| WO | 2014174182 A1 | 10/2014 | |
| WO | 2017077061 A1 | 5/2017 | |

OTHER PUBLICATIONS

Jiang J. et al., Comparison of Polyferric Sulphate with Other Coagulants for the Removal of Algae and Algae-Derived Organic Matter. Wat Sci Tech, Jun. 1, 1993, vol. 27, No. 11, pp. 221-230.
Grima E. M. et al., Recovery of microalgal biomass and metabolites: Process options and economics. Biotechnol Adv, Jan. 31, 2003, vol. 20, No. 7-8, pp. 491-515.
Wyatt et al., Critical Conditions for Ferric Chloride-Induced Flocculation of Freshwater Algae, Biotechnology and Bioengineering, vol. 109, No. 2, Feb. 2012, pp. 493-501.
Delauney et al., Biofouling protection for marine environmental sensors, Ocean Science, 6, 2010, 503-511.
Hanotou et al., Microflotation Performance for Algal Separation, Biotechnology and Bioengineering, 2012, vol. 109, No. 7, pp. 1663-1673.
Nordin et al., Interfacial Phenomena Governing Adhesion of Chlorella to Glass Surfaces, Biotechnology and Bioengineering, 1967, vol. IX, Issue 4, pp. 543-558.
Rakesh et al, Comparative evaluation of inorganic and organic amendments for their flocculation efficiency of selected microalgae, J Appl Phycol, 2014, 26:399-406.
Seo et al., Ferric chloride based downstream process for microalgae based biodiesel production, Bioresource Technology, 181, 2015, 143-147.

* cited by examiner

*Primary Examiner* — Ruth A Davis
(74) *Attorney, Agent, or Firm* — BCF LLP

(57) ABSTRACT

The present invention relates to a method for culturing microorganisms, in particular protists, carried out in such a way as to prevent the microorganisms from adhering to the walls of the reactors in which the culture is performed.

7 Claims, 3 Drawing Sheets

ANTI-ADHESION CULTURE MEDIUM

FIELD OF THE INVENTION

The present invention relates to a process for culturing microorganisms, in particular protists, carried out in such a way as to prevent the adhesion of the microorganisms to the walls of the reactors in which the culture is carried out.

BACKGROUND OF THE INVENTION

Microorganisms tend to adhere to the walls during long term cultures (from several days to several months). This phenomenon, known as fouling, is well known. It has very harmful consequences both on the productivity of the cultures and on the longevity of the equipment that must be cleaned regularly. The cells that adhere to the walls of the bioreactors reduce the amount of light penetrating inside, they can die for lack of resources (nutrients, oxygen, etc.) and thus cause the development of necrophagous organisms.

Some materials generate less adhesion than others, but none of them can overcome the above-mentioned disadvantages.

The salinity of the medium in which the microorganisms circulate and the nature of the wall containing it can affect the adhesion of the microorganisms to the wall. For example, it has been shown that the addition of iron chloride promotes the adhesion of microalgae of the genus *Chlorella* to glass walls (Nordin J. et al., 1967).

There are so-called active surface working methods such as mechanical scraper type systems (Wet Labs/Sea-Bird BioWiper), pressurized water jet, ultrasound, biocides such as chlorine or bromine (Alconox), anionic detergents for manual washing, UV radiation.

It is possible to build an integrated anti-fouling wall (YSI C-Spray). This can be a surface composed of a biocide that gradually releases the neutralizing element of the biofilm into the medium. These systems with biocides are usually composed of copper salts, it releases $Cu^{2+}$ which interferes with the enzymes on the membranes preventing their division (YSI 6-Series Anti-Fouling Kits).

These methods are difficult to implement because it is difficult to release the right amounts of products according to growth with a risk of biofilm developing too quickly. Once the biofilm has formed, the product is less effective. Moreover, the effectiveness of these chemical techniques is based on the death of the microalgae, thus to the detriment of their growth.

There remains the need for a means to avoid the aggregation of microorganisms grown in reactors while preserving or even improving the growth properties and biological activity of these microorganisms.

DISCLOSURE OF THE INVENTION

To solve this technical problem, the invention relates to the use of a flocculating agent in the culture medium during the cultivation of the microorganisms to prevent the adhesion of the microorganisms to the walls of the reactors in which the cultivation is carried out.

The invention also relates to a process for culturing microorganisms in a culture medium suitable for their growth, characterized in that the culture medium comprises a suitable amount of a flocculating agent to prevent the adhesion of the microorganisms to the walls of the reactors in which the culture is carried out.

DETAILED DESCRIPTION OF THE INVENTION

Figure 1:
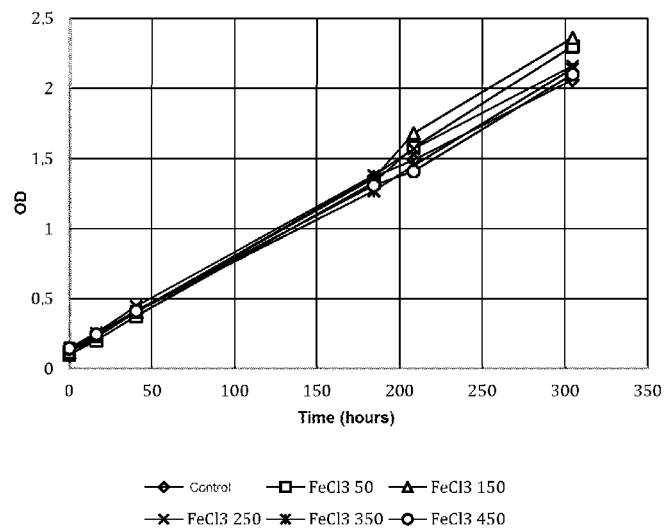
FIG. 1 shows the viability of microalgae with different concentrations of iron chloride.

The invention relates to the cultivation of microorganisms. These processes for the cultivation of microorganisms and the microorganisms cultivated are well known to the person skilled in the art.

These include bacteria, yeasts and protists, especially microalgae. According to a particular and preferred embodiment of the invention, the cultivated microorganisms are protists.

"Protists" refers to all eukaryotic unicellular microorganisms. Microalgae (Chlorophytes such as *Chlorella, Senedesmus, Tetraselmis, Haematococcus;* Charophytes, chrysophytes including diatoms; *Nannochloropsis;* Euglenophytes such as *Euglena, Phacus;* Rodophytes including *Galdieria*, etc.), unicellular fungi (Thrautochytrids such as *Schizochytrium, Aurantiochytrium*, etc.), cyanobacteria (*Anabaena, Nostoc, Microcistis, Arthrospira, Spirulina*, etc.) or heterotrophic *flagellates* (*Crypthecodinium* etc.) belong to the group of protists.

When the microalgae are of the genus *Chlorella*, they can be chosen among the species *C. acuminata, C. angustoellipsoidea, C. anitrata, C. antarctica, C. aureoviridis, C. autotrophica, C. botryoides, C. caldaria, C. candida, C. capsulate, C. chlorelloides, C. cladoniae, C. coelastroides, C. colonialis, C. communis, C. conductrix, C. conglomerata, C. desiccata, C. ellipsoidea, C. elongata, C. emersonii, C. faginea, C. fusca, C. glucotropha, C. homosphaera, C. infusionum, C. kessleri, C. koettlitzii, C. lacustris, C. lewinfi, C. lichina, C. lobophora, C. luteo-viridis, C. marina, C. miniata, C. minor, C. minutissima, C. mirabilis, C. mucosa, C. mutabilis, C. nocturna, C. nordstedtii, C. oblonga, C. oocystoides, C. ovalis, C. paramecfi, C. parasitica, C. parva, C. peruviana, C. photophila, C. pituita, C. pringsheimii, C. protothecoides, C. pulchelloides, C. pyrenoidosa, C. regularis, C. reisiglii, C. reniformis, C. rotunda, C. rubescens, C. rugosa, C. saccharophila, C. salina, C. simplex, C. singularis, C. sorokiniana, C. spaerckii, C. sphaerica, C. stigmatophora, C. subsphaerica, C. terricola, C. trebouxioides, C. vannielii, C. variabilis, C. viscosa, C. volutis, C. vulgaris, C. zopfingiensis*. Advantageously, according to the invention, the algae of the genus *Chlorella* can be algae chosen among the species *C. sorokiniana* or *C. vulgaris*.

When the microalgae are of the genus *Euglena*, they can be chosen among the species *E. viridis, E. gracilis, E. limosa, E. globosa, E. prowsei, E. polomorpha*.

When the microalgae are of the genus *Scenedesmus*, they may be selected from the species *S. abundans, S. aciculatus, S. aculeolatus, S. aculeotatus, S. acuminatus, S. acutiformis, S. acutus, S. aldavei, S. alternans, S. ambuehlii, S. anhuiensis, S. anomalus, S. antennatus, S. antillarum, S. apicaudatus, S. apiculatus, S. arcuatus, S. aristatus, S. armatus, S. arthrodesmiformis, S. arvernensis, S. asymmetricus, S. bacillaris, S. baculiformis, S. bajacalifomicus, S. balatonicus, S. basiliensis, S. bemardii, S. bicaudatus, S. bicellularis, S. bidentatus, S. bijuga, S. bijugatus, S. bijugus, S. brasiliensis, S. breviaculeatus, S. brevispina, S. caribeanus, S. carinatus, S. caudato-aculeolatus, S. caudatus, S. chlorelloides, S. circumfusus, S. coalitus, S. costatogranulatus, S. crassidentatus, S. curvatus, S. decorus, S. denticulatus, S. deserticola, S. diagonalis, S. dileticus, S. dimorphus, S. disciformis, S. dispar, S. distentus, S. ecornis, S. ellipsoideus, S. ellipticus, S. falcatus, S. fenestratus, S. flavescens, S. flexuosus, S. furcosus, S. fuscus, S. fusiformis, S. gracilis, S. graevenitzii, S. grahneisii, S. granulatus, S. gujaratensis, S. gutwinskii, S. hanleyi, S. helveticus, S. heteracanthus, S. hindakii, S. hirsutus, S. hortobagyi, S. houlensis, S. huangshanensis, S. hystrix, S. incrassatulus, S. indianensis, S. indicus, S. inermis, S. insignis, S. intermedius, S. javanensis, S. jovais, S. jugalis, S. kerguelensis, S. kissii, S. komarekii, S. lefevrei, S. linearis, S. littoralis, S. longispina, S. longus, S. luna, S. lunatus, S. magnus, S. maximus, S. microspina, S. minutus, S. mirus, S. morzinensis, S. multicauda, S. multiformis, S. multispina, S. multistriatus, S. naegelii, S. nanus, S. notatus, S. nygaardii, S. oahuensis, S. obliquus, S. obtusiusculus, S. obtusus, S. olvaltemus, S. oocystiformis, S. opoliensis, S. ornatus, S. ovaltemus, S. pannonicus, S. papfflosum, S. parisiensis, S. parvus, S. pecsensis, S. pectinatus, S. perforatus, S. planctonicus, S. plarydiscus, S. platydiscus, S. pleiomorphus, S. polessicus, S. polydenticulatus, S. polyglobulus, S. polyspinosus, S. praetervisus, S. prismaticus, S. producto-capitatus, S. protuberans, S. pseudoarmatus, S. pseudobemardii, S. pseudodenticulatus, S. pseudogranulatus, S. pseudohystrix, S. pyrus, S. quadrialatus, S. quadricauda, S. quadricaudata, S. quadricaudus, S. quadrispina, S. raciborskii, S. ralfsii, S. reginae, S. regularis, S. reniformis, S. rostrato-spinosus, S. rotundus, S. rubescens, S. scenedesmoides, S. schnepfii, S. schroeteri, S. securiformis, S. semicristatus, S. semipulcher, S. sempervirens, S. senilis, S. serrato-perforatus, S. serratus, S. serrulatus, S. setiferus, S. sihensis, S. smithii, S. soli, S. sooi, S. spicatus, S. spinoso-aculeolatus, S. spinosus, S. spinulatus, S. striatus., S. subspicatus, S. tenuispina, S. terrestris, S. tetradesmiformis, S. transilvanicus, S. tricostatus, S. tropicus, S. tschudyi, S. vacuolatus, S. variabilis, S. velitaris, S. verrucosus, S. vesiculosus, S. westii, S. weberi, S. wisconsinensis, S. wuhanensis, S. wuhuensis*. Advantageously, according to the invention, the algae of the genus *Scenedesmus* may be algae selected from the species *S. obliquus* or *S. abundans*.

When microalgae are diatoms, they may be selected from the following genera: *Nitzschia, Navicula, Gyrosigma, Phaeodactylum, Thalassiosira*, etc.

When the microalgae are of the genus *Nitzschia*, they may be selected from the species *N. abbreviata, N. abonuensis, N. abridia, N. accedens, N. accommodata, N. aciculariformis, N. acicularioides, N. acicularis* (including all these varieties), *N. acidoclinata, N. actinastroides, N. actydrophila, N. acula, N. acuminata* (including all these varieties), *N. acuta, N. adamata, N. adamatoides, N. adapta, N. adducta, N. adductoides, N. admissa, N. admissoides, N. aequalis, N. aequatorialis, N. aequora, N. aequorea, N. aerophila, N. aerophiloides, N. aestuari, N. affinis, N. africana, N. agnewii, N. agnita, N. alba, N. albicostalis, N. alexandrina, N. alicae, N. allanssonii, N. alpina, N. alpinobacillum, N. amabilis, N. ambigua, N. americana, N. amisaensis, N. amphibia, N. amphibia* (including all these varieties), *N. amphibioides, N. amphicephala, N. amphilepta, N. amphioxoides, N. amphioxys* (including all these varieties), *N. amphiplectans, N. amphiprora, N. amplectens, N. amundonii, N. anassae, N. andicola, N. angularis* (including all these varieties), *N. angulata, N. angustata* (including all these varieties), *N. angustatula, N. angustiforaminata, N. aniae, N. antarctica, N. antillarum, N. apiceconica, N. apiculata, N. archibaldii, N. arcuata, N. arcula, N. arcus, N. ardua, N. aremonica, N. arenosa, N. areolata, N. armoricana, N. asperula, N. astridiae, N. atomus, N. attenuata, N. aurantiaca, N. aurariae, N. aurica, N. auricula, N. australis, N. austriaca, N. bacata* (including all these varieties), *N. bacillariaeformis, N. baciffiformis, N. bacillum, N. balatonis, N. balcanica, N. baltica, N. barbieri* (including all these varieties), *N. barkleyi, N. barronii, N. barrowiana, N. bartholomei, N. bathurstensis, N. bavarica, N. behrei, N. bergii, N. beyeri, N. biacrula, N. bicapitata* (including all these varieties), *bicuneata, N. bifurcata, N. bilobata* (including all these varieties), *N. birostrata, N. bisculpta, N. bita, N. bizertensis, N. blankaartensis, N. bombiformis, N. borealis, N. bosumtwiensis, N. braarudii, N. brebissonii* (including all these varieties), *N. bremensis* (including all these varieties), *N. brevior, N. brevirostris, N. brevissima* (including all these varieties), *N. brevistriata, N. brightweffii, N. brittonii, N. brunoi, N. bryophila, N. buceros, N. bukensis, N. bulnheimiana, N. buschbeckii, N. calcicola, N. caledonensis, N. calida* (including all these varieties), *N. californica, N. campechiana, N. capensis, N. capitata, N. capitellata* (including all these varieties), *N. capuluspalae, N. carnicobarica, N. carnico-barica, N. challengeri, N. chalonii, N. chandolensis, N. chardezii, N. chasei, N. chauhanii, N. chungara, N. chutteri, N. circumsuta, N. clarissima, N. clausii, N. clementei, N. clementia, N. clevei, N. closterium* (including all these varieties), *N. coarctata, N. cocconeiformis, N. communis* (including all these varieties), *N. commutata, N. commutatoides, N. compacta, N. compressa* (including all these varieties), *N. concordia, N. confinis, N. conformata, N. confusa, N. congolensis, N. constricta* (including all these varieties), *N. consummata, N. corpulenta, N. costei, N. coutei, N. creticola, N. cucumis, N. cursoria, N. curta, N. curvata, N. curvilineata, N. curvipunctata, N. curvirostris* (including all these varieties), *N. curvula* (including all these varieties), *N. cuspidata, N. cylindriformis, N. cylindrus, N. dakariensis, N. davidsonii, N. dealpina, N. debilis, N. decipiens, N. delauneyi, N. delicatissima, N. delicatula, N. delognei, N. denticula* (including all these varieties), *N. denticuloides, N. desertorum, N. dianae, N. diaphana, N. diducta, N. didyma, N. dietrichii, N. dilatata, N. diluviana, N. dippelii, N. directa, N. diserta, N. disputata, N. dissipata* (including all these varieties), *N. dissipatoides, N. distans* (including all these varieties), *N. distantoides, N. divaricata, N. divergens, N. diversa, N. diversecostata, N. doljensis, N. draveillensis, N. droebakensis, N. dubia* (including all these varieties), *N. dubiformis, N. dubioides, N. ebroicensis, N. eglei, N. elegans, N. elegantula, N. elegens, N. elliptica, N. elongata, N. entomon, N. epiphytica, N. epiphyticoides, N. epithemiformis, N. epithemioides, N. epithemoides* (including all these varieties), *N. epsilon, N. erlandssonii, N. erosa, N. etoshensis, N. examinanda, N. eximia, N. famelica, N. fasciculata, N. febigeri, N. ferox, N. ferrazae, N. fibula-fissa, N. filiformis* (including all these varieties), *N. flexa, N. flexoides, N. fluminensis, N. fluorescens, N. fluvialis, N. fogedii, N. fonticola* (including all these varieties), *N. fonticoloides, N. fonticula, N. fon-*

*tifuga, N. forfica, N. formosa, N. fossalis, N. fossilis, N. fragilariiformis, N. franconica, N. fraudulenta, N. frauenfeldii, N. frequens, N. frickei, N. frigida* (including all these varieties), *N. frustuloides, N. frustulum* (including all these varieties), *N. fruticosa, N. fundi, N. fusiformis, N. gaarderi, N. gaertnerae, N. gandersheimiensis, N. garrensis, N. gazellae, N. geitleri, N. geitlerii, N. gelida* (including all these varieties), *N. geniculata, N. gessneri, N. gieskesii, N. gigantea, N. gisela, N. glabra, N. glacialis* (including all these varieties), *N. glandiformis, N. goetzeana* (including all these varieties), *N. gotlandica, N. graciliformis, N. gracilis* (including all these varieties), *N. graciffima, N. graciloides, N. gradifera, N. graeffii, N. grana, N. grandis, N. granii* (including all these varieties), *N. granulata* (including all these varieties), *N. granulosa, N. groenlandica, N. grossestriata, N. grovel, N. gruendleri, N. grunowii, N. guadalupensis, N. guineensis, N. guttula, N. gyrosigma, N. habirshawii, N. habishawii, N. hadriatica, N. halteriformis, N. hamburgiensis, N. hantzschiana* (including all these varieties), *N. harderi, N. harrissonii, N. hassiaca, N. heidenii, N. heimii, N. hemistriata, N. heteropolica, N. heuflerania, N. heufleriana* (including all these varieties), *N. hiemalis, N. hiengheneana, N. hierosolymitana, N. hoehnkii, N. holastica, N. hollerupensis, N. holsatica, N. homburgiensis, N. hudsonii, N. hummii, N. hungarica* (including all these varieties), *N. hustedti, N. hustedtiana, N. hyalina, N. hybrida* (including all these varieties), *N. hybridaeformis, N. ignorata* (including all these varieties), *N. iltisii, N. impressa, N. improvisa, N. incerta, N. incognita, N. inconspicua, N. incrustans, N. incurva* (including all these varieties), *N. indica, N. indistincta, N. inducta, N. inflatula, N. ingenua, N. inimasta, N. innominata, N. insecta, N. insignis* (including all these varieties), *N. intermedia* (including all these varieties), *N. intermissa, N. interrupta, N. interruptestriata, N. invicta* (including all these varieties), *N. invisa, N. invisitata, N. iranica, N. irregularis, N. irremissa, N. irrepta, N. irresoluta, N. irritans, N. italica, N. janischii, N. jelineckii, N. johnmartinii, N. Juba, N. jucunda, N. jugata* (including all these varieties), *N. jugiformis, N. kahlii, N. kanakarum, N. kanayae, N. kavirondoensis, N. kerguelensis, N. kimberliensis, N. kittlii, N. kittonii, N. knysnensis, N. kolaczeckii, N. kotschyi, N. kowiensis, N. krachiensis, N. krenicola, N. kuetzingiana* (including all these varieties), *N. kuetzingii, N. kuetzingioides, N. kurzeana, N. kurzii, N. kützingiana* (including all these varieties), *N. labella, N. labuensis, N. lacrima, N. lacunarum, N. lacunicola, N. lacus-karluki, N. lacustris, N. lacuum, N. laevis, N. laevissima, N. lagunae, N. lagunensis, N. lamprocampa* (including all these varieties), *N. lanceola* (including all these varieties), *N. lanceolata* (including all these varieties), *N. lancettula, N. lancettuloides, N. lange-bertalotii, N. latens, N. latestriata, N. latiuscula, N. lauenbergiana, N. lauenburgiana, N. lecointei, N. leehyi, N. legleri, N. lehyi, N. leistikowii, N. lesbia, N. lesinensis, N. lesothensis, N. leucosigma, N. levidensis* (including all these varieties), *N. liebetruthii* (including all these varieties), *N. ligowskii, N. limicola, N. limulus, N. linearis* (including all these varieties), *N. lineata, N. lineola, N. linkei, N. lionella, N. littoralis* (including all these varieties), *N. littorea, N. longa, N. longicollum, N. longirostris, N. longissima* (including all these varieties), *N. lorenziana* (including all these varieties), *N. lucisensibilis, N. lunaris, N. lunata, N. lurida, N. luzonensis, N. macaronesica, N. macedonica, N. macera, N. machardyae, N. macilenta* (including all these varieties), *N. magnacarina, N. mahihaensis, N. mahoodii, N. maillardii, N. major, N. majuscula* (including all these varieties), *N. makarovae, N. manca, N. mancoides, N. manguini, N. marginata, N. marginulata* (including all these varieties), *N. marina, N. martiana, N. maxima, N. media, N. medioconstricta, N. mediocris, N. mediterranea, N. metzeltinii, N. microcephala* (including all these varieties), *N. migrans, N. minuta, N. minutissima, N. minutula, N. miramarensis, N. miserabilis, N. mitcheffiana, N. modesta, N. moissacensis* (including all these varieties), *N. mollis, N. monachorum, N. monoensis, N. montanestris, N. morosa, N. multistriata, N. nana, N. natalensis, N. natans, N. nathorsti, N. navicularis, N. navis-varingica, N. navrongensis, N. neglecta, N. nelsonii, N. neocaledonica, N. neoconstricta, N. neofrigida, N. neogena, N. neotropica, N. nereidis, N. nicobarica, N. nienhuisii, N. normannii, N. notabilis, N. nova, N. novae-guineaensis, N. novae-guineensis, N. novaehollandiae, N. nova-zealandia, N. nyassensis, N. oberheimiana, N. obesa, N. obliquecostata, N. obscura, N. obscurepunctata, N. obsidialis, N. obsoleta, N. obsoletiformis, N. obtusa* (including all these varieties), *N. obtusangula, N. oceanica, N. ocellata, N. oliffi, N. omega, N. osmophila, N. ossiformis, N. ostenfeldii, N. ovalis, N. paaschei, N. pacifica, N. palacea, N. palea* (including all these varieties), *N. paleacea, N. paleaeformis, N. paleoides, N. palustris, N. pamirensis, N. panduriformis* (including all these varieties), *N. pantocsekii, N. paradoxa* (including all these varieties), *N. parallela, N. pararostrata, N. partita, N. parvula* (including all these varieties), *N. parvuloides, N. paxiffifer, N. peisonis, N. pelagica, N. pellucida, N. pennata, N. peragaffii, N. perindistincta, N. perminuta, N. perpusilla* (including all these varieties), *N. perspicua, N. persuadens, N. pertica, N. perversa, N. petitiana, N. philippinarum, N. pilum, N. pinguescens, N. piscinarum, N. plana* (including all these varieties), *N. planctonica, N. plicatula, N. pliovetterana, N. polaris, N. polymorpha, N. ponciensis, N. praecurta, N. praefossilis, N. praereinholdii, N. princeps, N. procera, N. prolongata* (including all these varieties), *N. prolongatoides, N. promare, N. propinqua, N. pseudepiphytica, N. pseudoamphioxoides, N. pseudoamphioxys, N. pseudoamphyoxys, N. pseudoatomus, N. pseudobacata, N. pseudocapitata, N. pseudocarinata, N. pseudocommunis, N. pseudocylindrica, N. pseudodelicatissima, N. pseudofonticola, N. pseudohungarica, N. pseudohybrida, N. pseudonana, N. pseudoseriata, N. pseudosigma, N. pseudosinuata, N. pseudostagnorum, N. pubens, N. pulcherrima, N. pumila, N. punctata* (including all these varieties), *N. pungens* (including all these varieties), *N. pungiformis, N. pura, N. puriformis, N. pusilla* (including all these varieties), *N. putrida, N. quadrangula, N. quickiana, N. rabenhorstii, N. radicula* (including all these varieties), *N. rautenbachiae, N. recta* (including all these varieties), *N. rectiformis, N. rectilonga, N. rectirobusta, N. rectissima, N. regula, N. reimeri, N. reimerii, N. reimersenii, N. retusa, N. reversa, N. rhombica, N. rhombiformis, N. rhopalodioides, N. richterae, N. rigida* (including all these varieties), *N. ritscheri, N. robusta, N. rochensis, N. rolandii, N. romana, N. romanoides, N. romanowiana, N. rorida, N. rosenstockii, N. rostellata, N. rostrata, N. ruda, N. rugosa, N. rupestris, N. rusingae, N. ruttneri, N. salinarum, N. salinicola, N. salpaespinosae, N. salvadoriana, N. sansimoni, N. sarcophagum, N. scabra, N. scalaris, N. scaligera, N. scalpeffiformis, N. schoenfeldii, N. schwabei, N. schweikertii, N. scutellum, N. seffingii, N. semicostata, N. semirobusta, N. separanda, N. seriata* (including all these varieties), *N. serpenticola, N. serpentiraphe, N. serrata, N. sibula* (including all these varieties), *N. sigma* (including all these varieties), *N. sigmaformis, N. sigmatella, N. sigmoidea* (including all these varieties), *N. silica, N. silicula* (including all these varieties), *N. siliqua, N. similis, N. simplex, N. simpliciformis, N. sinensis, N. sinuata* (including all these varieties), *N. smithii, N. socia-*

*bilis*, *N. socialis* (including all these varieties), *N. solgensis*, *N. solida*, *N. solita*, *N. soratensis*, *N.* sp., *N. spathulata* (including all these varieties), *N. speciosa*, *N. spectabilis* (including all these varieties), *N. sphaerophora*, *N. spiculoides*, *N. spiculum*, *N. spinarum*, *N. spinifera*, *N. stagnorum*, *N. steenbergensis*, *N. stellata*, *N. steynii*, *N. stimulus*, *N. stoliczkiana*, *N. stompsii* (including all these varieties), *N. strelnikovae*, *N. stricta*, *N. strigillata*, *N. striolata*, *N. subaccommodata*, *N. subacicularis*, *N. subacuta*, *N. subamphioxioides*, *N. subapiculata*, *N. subbacata*, *N. subcapitata*, *N. subcapitellata*, *N. subcohaerens* (including all these varieties), *N. subcommunis*, *N. subconstricta*, *N. subcurvata*, *N. subdenticula*, *N. subfalcata*, *N. subfraudulenta*, *N. subfrequens*, *N. subfrustulum*, *N. subgraciloides*, *N. subinflata*, *N. subinvicta*, *N. sublaevis*, *N. sublanceolata*, *N. sublica*, *N. sublinearis*, *N. sublongirostris*, *N. submarina*, *N. submediocris*, *N. subodiosa*, *N. subpacifica*, *N. subpunctata*, *N. subromana*, *N. subrostrata*, *N. subrostratoides*, *N. subrostroides*, *N. subsalsa*, *N. subtilioides*, *N. subtilis* (including all these varieties), *N. subtubicola*, *N. subvitrea*, *N. suchlandtii*, *N. sulcata*, *N. sundaensis*, *N. supralitorea*, *N. tabellaria*, *N. taenia*, *N. taeniiformis*, *N. tantata*, *N. tarda*, *N. taylorii*, *N. temperei*, *N. tenella*, *N. tenerifa*, *N. tenuiarcuata*, *N. tenuirostris*, *N. tenuis* (including all these varieties), *N. tenuissima*, *N. tergestina*, *N. terrestris*, *N. terricola*, *N. thermalis* (including all these varieties), *N. thermaloides*, *N. tibetana*, *N. tirstrupensis*, *N. tonoensis*, *N. towutensis*, *N. translucida*, *N. tropica*, *N. tryblionella* (including all these varieties), *N. tsarenkoi*, *N. tubicola*, *N. tumida*, *N. turgidula*, *N. turgiduloides*, *N. umaoiensis*, *N. umbilicata*, *N. umbonata*, *N. vacillata*, *N. vacua*, *N. valdecostata*, *N. valdestriata*, *N. valens*, *N. valga*, *N. valida* (including all these varieties), *N. vanheurckii*, *N. vanoyei*, *N. vasta*, *N. ventricosa*, *N. vermicularioides*, *N. vermicularis* (including all these varieties), *N. vermicularoides*, *N. vexans*, *N. victoriae*, *N. vidovichii*, *N. vildaryana*, *N. villarealii*, *N. virgata*, *N. visurgis*, *N. vitrea* (including all these varieties), *N. vivax* (including all these varieties), *N. vixnegligenda*, *N. vonhauseniae*, *N. vulga*, *N. weaveri*, *N. weissflogii*, *N. westii*, *N. williamsiii*, *N. wipplingeri*, *N. witkowskii*, *N. wodensis*, *N. woltereckii*, *N. woltereckoides*, *N. wuellerstorfii*, *N. wunsamiae*, *N. yunchengensis*, *N. zebuana*, *N. zululandica*.

Advantageously according to the invention, the algae of the genus *Nitzschia* may be algae selected from the species *N.* sp.

Where the microalgae are of the genus *Haematococcus*, they may be selected from the species *H. allmanii*, *H. buetschlii*, *H. capensis*, *H. carocellus*, *H. droebakensis*, *H. grevilei*, *H. insignis*, *H. lacustris*, *H. murorum*, *H. pluvialis*, *H. salinus*, *H, sanguineis*, *H. thermalis*, *H. zimbabwiensis*.

When the microalgae are of the genus *Aurantiochytrium*, they may be selected from the species: *A. limacinum*, *A. mangrovei*.

When the microalgae are of the genus *Schizochytrium*, they may be selected from the species: *S. aggregatum*, *S. limacinum*, *S. mangrovei*, *S. minutum*, *S. octosporum*.

When the microalgae are of the genus *Crypthecodinium*, they may be selected from the species: *C. cohnii*, *C. setense*.

When the microalgae are of the genus *Tetraselmis*, they may be selected from the species: *T. alacris*, *T. apiculata*, *T. amoldii*, *T. ascus*, *T. astigmatica*, *T. bichlora*, *T. bilobata*, *T. bolosiana*, *T. chui*, *T. contracta*, *T. convolutae*, *T. cordiformis*, *T. desikacharyi*, *T. elliptica*, *T. fontiana*, *T. gracilis*, *T. hazenii*, *T. helgolandica*, *T. impellucida*, *T. incisa*, *T. inconspicua*, *T. indica*, *T. levis*, *T. maculata*, *T. marina*, *T. mediterranea*, *T. micropapillata*, *T. rubens*, *T. striata*, *T. subcordiformis*, *T. suecica*, *T. tetrabrachia*, *T. tetrathele*, *T. verrucosa*, *T. viridis*, *T. wettsteinii*.

According to a particular embodiment of the invention, the protists are selected from those of the genera *Chlorella*, *Galdieria*, *Euglena*, cyanobacteria and diatoms.

Microorganism culture methods are also well known to the skilled person, whether in auxotrophic, heterotrophic or mixotrophic mode (references). The culture media used for these different culture modes adapted to the different microorganisms mentioned above are also well known to the person skilled in the art (reference).

The invention is particularly suitable for so-called long-term cultures (from several days to several months), subject to the phenomenon of adhesion of microorganisms to the walls of the reactors in which they are cultivated.

The reactors used for these different methods of cultivation are also well known to the skilled person, such as in bubble columns, airlifts (Lesson: Industrial Applications of Microbes, Dr. Parvinder Kaur, page 11-12), fermenters (Tryton™), tubular photobioreactors (Schott, Synoxis Algae), raceways and bioreactors.

The walls of the bioreactors are made of materials known to the person skilled in the art, such as flexible plastic, stainless steel, concrete or brick.

The invention is particularly suitable for cultures carried out in reactors comprising at least one transparent wall to allow light to pass through, whether it is natural or artificial light, in autotrophic or mixotrophic mode.

The light-transparent walls, which are well known to the skilled person, can be made of glass, borosilicate, plastic such as polymethyl methacrylate (PMMA), polyvinyl chloride (PVC), polyethylene (PE), in particular low-density polyethylene (LDPE), polycarbonate, polystyrene (PS). The transparent walls are advantageously made of PMMA, PVC, PE or polycarbonate.

The invention is particularly suitable for transparent wall reactors of the bubble column type in autotrophic mode for the culture of microalgae, such as carbon sinks. These carbon sinks are bubble columns or "air lifts" for growing microalgae in an auxotrophic mode and in which the ambient air is passed through and the carbon dioxide is absorbed by the microorganisms as a carbon source. As they multiply, they depollute the atmosphere by absorbing carbon dioxide. Such systems are notably described in WO 2014/063229 or WO 2017/077061.

Microalgae need light in order to divide. The availability of light in the environment is essential for the development of microalgae. However, adhesion to the reactor walls reduces the available light and the growth capacities, and therefore the carbon absorption capacity of the microalgae.

The carbon sink corresponds to a column of variable volume containing microalgae that will be able to capture between 1 and 10 000 tons of $CO_2$ per year.

In some cases, the light does not come from outside the bioreactor through transparent walls but is brought inside the bioreactor by submersing sealed light sources in the vessel. For example, a lighted counter-baffle system can be used (WO2014/174182). Then, the invention makes it possible to reduce the adhesion of the cells to the light source.

By limiting adhesion, light availability in the bioreactor is increased. As a result, the microalgae maintain their growth capacity and column cleaning costs are reduced.

The microalgae used in these carbon sinks are generally selected from chlorophyllous and non-chlorophyllous microalgae but also from other microorganisms that generally have negative outer membranes. These microorganisms generally having negative outer membranes and capable of being used in carbon sinks are well known to the person skilled in the art, especially those of the genera *Chlorella, Galdieria, Euglena*, cyanobacteria and diatoms.

The culture medium used includes "BG-11 growth media", described and marketed by UTEX (UTEX Culture Collection of Algae, 205 W. 24th St, Biological Labs 218, The University of Texas at Austin (F0402), Austin, TX 78712 USA). For autotrophic culture, the culture medium does not include any carbon source other than carbon dioxide from the air passing through the culture medium. However, to initiate or restart microalgal growth, a carbon source other than carbon dioxide, such as glucose, may be temporarily added.

The ambient air flow rate in the culture medium corresponds to a flow rate ranging from 0.3 to 0.5 vvm. Outside air containing $CO_2$ passes through a bubbler to be injected into the column. The injected air can also come from plant fumes (for example from incineration plants) which contain between 1 and 20% $CO_2$.

When the maximum amount of biomass is reached, the carbon sink is drained. Finally, the sink is filled again with medium to be inoculated with microalgae.

Flocculating agents are well known to the person skilled in the art. They are generally used at the end of the culture of microorganisms, added to the fermentation must when the culture is finished to facilitate the separation of the biomass from the culture medium (Hanotu J. et al., 2012). These additions after the culture is completed are generally not detrimental to the use of the recovered microalgae, for example for aquaculture feeds (US 2013/205850).

These flocculating agents are organic or inorganic, such as chitosan, arboxymethylcelluloses, starches or starch derivatives such as rice starch, corn starch, tapioca starch, yellow dextrin, potato starch, pregelatinized starch or cationic starch for organic flocculants, or aluminum sulfate, calcium chloride, zinc chloride or iron chloride for inorganic flocculants.

Unlike the uses of the prior art, the use of the flocculating agents according to the invention is done during cultivation, in the culture medium, not to promote the separation of the biomass from the culture medium, but to promote the maintenance of this biomass in the culture medium by preventing its adhesion to the walls of the reactors.

Figure 2:
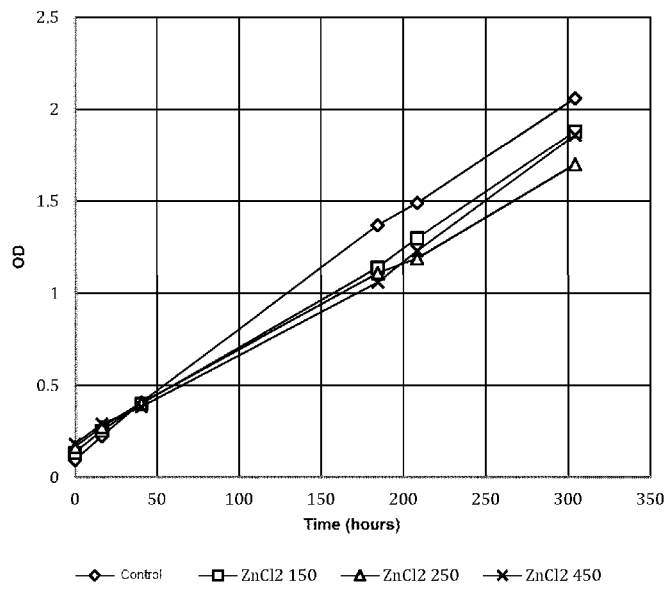
FIG. 2 shows the viability of microalgae with different concentrations of zinc chloride.
Figure 3:
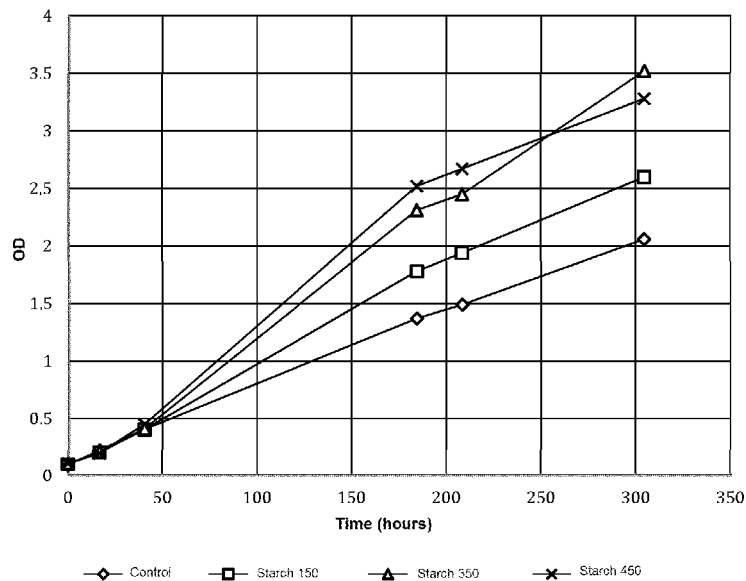
FIG. 3 shows the viability of microalgae with different concentrations of starch.

The flocculating agents according to the invention must be able to be used without affecting the growth capacities and biological activity of the cultivated microorganisms. Indeed, viability tests have shown that the flocculating agents and iron chloride in particular do not disturb the growth of microalgae. (FIGS. 1, 2 and 3)

The skilled person will know how to select, by simple laboratory tests, the flocculating agents best suited to the microorganisms cultivated and their growing conditions.

Preferably, the flocculating agents used in the growing medium according to the invention are selected from zinc chloride and iron chloride, more preferentially iron chloride. These flocculating agents are commercially available, in particular under the names iron(III) chloride, ferric chloride, iron perchloride from suppliers such as VWR and Sigma.

The skilled person will be able to determine by simple laboratory tests the appropriate amount of flocculating agent necessary to prevent the adhesion of microorganisms to the walls.

The person skilled in the art will know how to determine the quantity of flocculant to be added, in particular to obtain a flocculation efficiency (percentage of sedimented biomass relative to the total biomass) of at least 10%, advantageously of at least 30%. Indeed, the flocculation efficiency changes according to the flocculant for the same concentration. The composition of the culture medium and the strain of microorganism used can also have an impact on the flocculation efficiency. These adjustments are part of the routine development work known to the skilled person.

Advantageously, the amount of flocculating agent in the culture medium ranges from 50 to 450 mg/L, more particularly from 150 to 350 mg/L.

The addition of flocculating agents to the culture medium can lead to the formation of suspended cell aggregates. In order to prevent or limit this formation of aggregates, the culture should be carried out under normal conditions of agitation, such as mechanical or passive agitation such as in a bubble column or an air lift reactor.

The addition of flocculating agent to the culture medium can be done at any time during the culture to prevent or limit the formation of adhesion on the reactor walls. Preferably, the flocculating agent is added to the culture medium at the beginning of the culture process and maintained in the culture medium until the end of the culture.

The invention also relates to a culture medium suitable for the culture of microorganisms, characterized in that it comprises from 50 to 450 mg/L, more particularly from 150 to 350 mg/L of flocculating agent as defined above, in particular iron chloride.

EXAMPLES

Two microalgae cultures, one control without the flocculating agent and one with the flocculating agent $FeCl_3$ are carried out.

Materials and Methods

Microalgae

The microalgae used in this example come from the species *Chlorella sorokiniana*.

Culture Medium

BG-11 growth media (UTEX) was used.

Culture Conditions

The columns were inoculated with 0.5 g/L of microalgae. The temperature remained constant at 30° C. Brightness was set at 500 µEinstein/m$^2$/s. The pH was stabilized at 6.3 up to 160 hours (control) 189 hours ($FeCl_3$) and then was not regulated, the pH was raised to 8 to stabilize at this level until the end of the experiment. It was chosen not to regulate the pH any further because a high pH increases the ability of microalgae to stick to the walls.

Biomass Recovery

The biomass is recovered with a pump, the biomass in suspension is obtained as well as the biomass remaining at the bottom of the column. Then a volume of water is added to the column in order to loosen the microalgae remaining on the walls. A dry mass measurement is carried out on each batch.

Passage of Light

Figure 5:
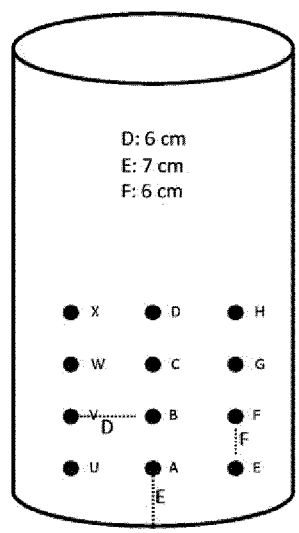
FIG. 5 shows the points on the wall of the transparent column used as a reactor for measuring the capacity of light to pass through the column.
Figure 6:
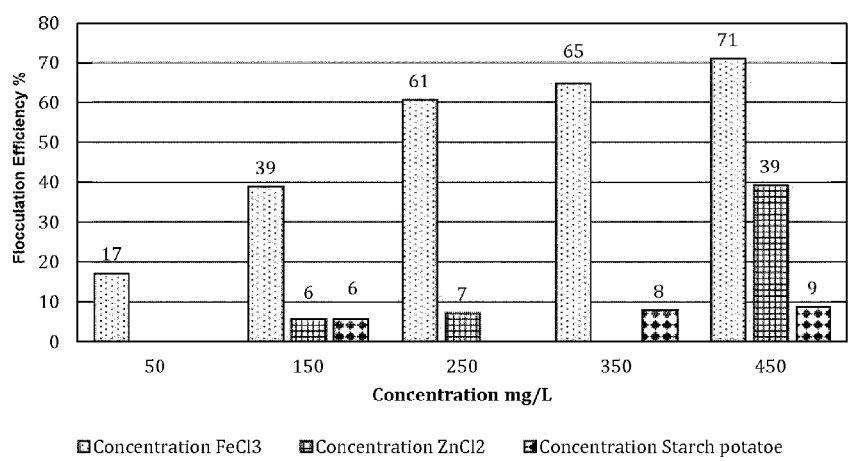
FIG. 6 shows the effectiveness of three flocculants. These are two inorganic elements, $FeCl_3$ and $ZnCl_2$, and one organic element, potato starch.

The analysis of the capacity of light to pass through the column is measured at 24 points arranged on the column wall as shown in FIG. 5. These measurements are expressed in µEinstein/m$^2$/s.

Results

Figure 4:
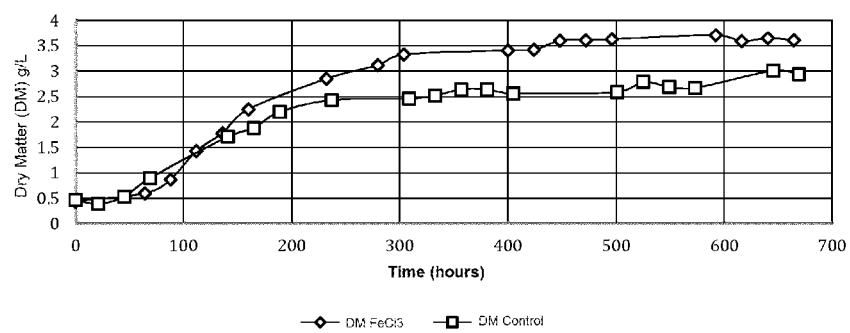
FIG. 4 shows the biomass production of the same microalgae under two conditions, with and without the flocculating agent $FeCl_3$. The temperature, pH, luminosity conditions are the same.

FIG. 4 shows the difference in biomass production with and without flocculating agent. For the experiment with the flocculant, it can be seen that up to 1 g/L of additional biomass is produced in the culture medium compared to the same culture without the flocculating agent. This additional biomass is due to the failure of the microalgae to stick to the wall.

At the end of the experiment a distinction is made between the biomass in the growing medium and the biomass adhered to the walls.

In the $FeCl_3$-free experiment, the total suspended biomass in the medium was 14.7 g and the biomass remaining at the bottom of the column was 5.6 g. The biomass adhered to the walls is 1.013 g, which represents 4.74% of the total biomass.

In the experiment with $FeCl_3$, the total biomass suspended in the medium was 18 g and the biomass remaining at the bottom of the column was 1.11 g. The biomass adhered to the walls is 0.043 g, which represents 0.22% of the total biomass.

A greater amount of suspended biomass was observed with the use of $FeCl_3$, or 94% of the suspended biomass compared to 69% in the control.

TABLE 1

Proportion of DM in the 3 areas of the column

|  | Control (g) | Control % Biomass | $FeCl_3$ (g) | $FeCl_3$ % Biomass |
| --- | --- | --- | --- | --- |
| DM Medium | 14.700 | 68.769 | 18.050 | 94.17 |
| DM at bottom | 5.663 | 26.492 | 1.075 | 5.61 |
| DM wall | 1.013 | 4.739 | 0.043 | 0.22 |
| Total | 21.376 | 100.000 | 19.168 | 100.00 |

The results of the analysis of the passage of light through the walls of the column are given in Table 2 below.

Light measurements were made on 24 points as shown in the schematic representation of the column in FIG. 5. The light was measured on a clean column without microalgae, a control column with microalgae and a $FeCl_3$ containing column with microalgae.

TABLE 2

Measurement of 24 points on the column

| Point | μmol per point Control | μmol per point $FeCl_3$ | μmol per point clean column | Difference $FeCl_3$ % | Difference Control % |
| --- | --- | --- | --- | --- | --- |
| A | 120 | 214 | 295 | −27.46 | −59.32 |
| B | 125 | 252 | 314 | −19.75 | −60.19 |
| C | 236 | 232 | 289 | −19.72 | −18.34 |
| D | 200 | 198 | 228 | −13.16 | −12.28 |
| E | 13 | 204 | 287 | −28.92 | −95.47 |
| F | 109 | 263 | 298 | −11.74 | −63.42 |
| G | 189 | 248 | 274 | −9.49 | −31.02 |
| H | 128 | 192 | 225 | −14.67 | −43.11 |
| I | 143 | 233 | 307 | −24.10 | −53.42 |
| J | 213 | 254 | 317 | −19.87 | −32.81 |
| K | 223 | 236 | 270 | −12.59 | −17.41 |
| L | 191 | 189 | 225 | −16.00 | −15.11 |
| M | 143 | 244 | 302 | −19.21 | −52.65 |
| N | 200 | 256 | 297 | −13.80 | −32.66 |
| O | 204 | 233 | 262 | −11.07 | −22.14 |
| P | 175 | 190 | 212 | −10.38 | −17.45 |
| Q | 156 | 246 | 291 | −15.46 | −46.39 |
| R | 199 | 257 | 299 | −14.05 | −33.44 |
| S | 198 | 235 | 268 | −12.31 | −26.12 |
| T | 175 | 186 | 223 | −16.59 | −21.52 |
| U | 123 | 196 | 293 | −33.11 | −58.02 |
| V | 199 | 242 | 302 | −19.87 | −34.11 |

TABLE 2-continued

Measurement of 24 points on the column

| Point | μmol per point Control | μmol per point $FeCl_3$ | μmol per point clean column | Difference $FeCl_3$ % | Difference Control % |
| --- | --- | --- | --- | --- | --- |
| W | 222 | 226 | 280 | −19.29 | −20.71 |
| X | 193 | 185 | 228 | −18.86 | −15.35 |
|  |  |  | Average | −17.56 | −36.77 |

On the 12 points that make up the lower part of the column, light penetration is 2.78 times greater with the presence of $FeCl_3$.

TABLE 3

Measurement of the 12 points of the lower half of the column

| Point | μmol per point Control | μmol per point $FeCl_3$ | FeCl3/Control |
| --- | --- | --- | --- |
| A | 120 | 214 | 1.78 |
| B | 125 | 252 | 2.02 |
| E | 13 | 204 | 15.69 |
| F | 109 | 263 | 2.41 |
| I | 143 | 233 | 1.63 |
| J | 213 | 254 | 1.19 |
| M | 143 | 244 | 1.71 |
|  |  | Average | 3.78 |

The whole of the results show an improvement in the cultures of microorganisms due to the presence of a flocculating agent in the culture medium, due to the prevention of the adhesion of the microorganisms on the reactor walls.

Similar results will be obtained with other microorganisms under other culture conditions in heterotrophic or mixotrophic mode, especially in the case of long-term cultures, in particular for the culture of *Chlorella, Galdieria, Euglena*, cyanobacteria, diatoms.

REFERENCES

L. Delauney, C. Compere & M. Lehaitre, Biofouling protection for marine environmental sensors—Ocean Science, 6, 503-511, 2010

J. Hanotu, H. C. Hemaka Bandulasena & W. B. Zimmerman, Microflotation Performance for Algal Separation, Biotechnology and Bioengineering, 2012; 109:7, 1663-1673

J. S. Nordin, H. M. Tsuchiya & A. G. Fredrickson, Interfacial Phenomena Governing Adhesion of *Chlorella* to Glass Surfaces, Biotechnology and Bioengineering, 1967; IX, 545-558

Nicholas B. Wyatt, Lindsey M. Gloe, Patrick V. Brady, John C. Hewson, Anne M. Grillet, Matthew G. Hankins & Phillip I. Pohl, Critical Conditions for Ferric Chloride-Induced Flocculation of Freshwater Algae—Biotechnol. Bioeng. 2012; 109: 493-501.

Suchitra Rakesh, Sudhir Saxena, Dolly W. Dhar, Radha Prasanna & Anil K. Saxena, Comparative evaluation of inorganic and organic amendments for their flocculation efficiency of selected microalgae—Springer Science+Business Media Dordrecht 2013

Yeong Hwan Seo, Mina Sung, Bohwa Kim & Jong-In Han, Ferric chloride based downstream process for microalgae based biodiesel production—DOI: 10.1016/j.biortech.2015.01.004

WO 2014/063229
WO 2014/174182
WO 2017/077061
US 2013/205850

The invention claimed is:

1. A process for culturing microorganisms in a culture medium suitable for their growth, wherein the culture medium comprises between 50 mg/L and 450 mg/L of a flocculating agent during a culture phase to prevent adhesion of the microorganisms to the walls of the reactors in which the culture is carried out, the microorganisms being microalgae of the genus *Chlorella*, and the flocculating agent being selected from iron chloride and zinc chloride; and wherein the culture is a long-term culture of at least 50 hours.

2. The process according to claim 1, wherein the flocculating agent is added to the culture medium at the beginning of the culture and maintained until the end of the culture.

3. The process according to claim 1, wherein the reactor is a carbon sink.

4. The process according to claim 1, wherein the culture is carried out in autotrophic mode or in mixotrophic mode and the reactor comprises at least one wall that is transparent to light.

5. The process according to claim 4, wherein the wall is polymethyl methacrylate (PMMA), polyvinyl chloride (PVC), polyethylene (PE) or polycarbonate.

6. The process according to claim 1, wherein the flocculation efficiency is of at least 10%.

7. The process according to claim 6, wherein the flocculation efficiency is of at least 30%.

* * * * *